(12) United States Patent
Ibrahim (10) Patent No.: US 8,452,412 B2
(45) Date of Patent: May 28, 2013

(54) MEASUREMENT OF TRANSMITTER/RECEIVER SEPARATION

(75) Inventor: Ibrahim H. Ibrahim, North Ryde (AU)

(73) Assignee: Cochlear Limited, Macquarie University, NSW (AU)

( * ) Notice: Subject to any disclaimer, the term of this patent is extended or adjusted under 35 U.S.C. 154(b) by 1572 days.

(21) Appl. No.: 10/526,493

(22) PCT Filed: Sep. 4, 2003

(86) PCT No.: PCT/AU03/01140
§ 371 (c)(1),
(2), (4) Date: Mar. 30, 2006

(87) PCT Pub. No.: WO2004/021876
PCT Pub. Date: Mar. 18, 2004

(65) Prior Publication Data
US 2007/0100395 A1    May 3, 2007

(30) Foreign Application Priority Data
Sep. 4, 2002  (AU) .................................. 2002951217

(51) Int. Cl.
*A61N 1/375*    (2006.01)
(52) U.S. Cl.
USPC ............... 607/60; 607/31; 607/32; 607/61

(58) Field of Classification Search
USPC .................................. 607/30–33, 60, 61
See application file for complete search history.

(56) References Cited

U.S. PATENT DOCUMENTS

| | | | |
|---|---|---|---|
| 5,314,453 A * | 5/1994 | Jeutter | 607/60 |
| 6,088,619 A | 7/2000 | Hein et al. | |
| 6,138,681 A * | 10/2000 | Chen et al. | 128/899 |
| 6,212,431 B1 | 4/2001 | Hahn et al. | |
| 6,366,817 B1 * | 4/2002 | Kung | 607/61 |
| 2003/0074035 A1 * | 4/2003 | Bornhoft et al. | 607/60 |

FOREIGN PATENT DOCUMENTS

| | | |
|---|---|---|
| WO | WO 99/18879 | 4/1999 |
| WO | WO 02/02005 | 1/2002 |

* cited by examiner

*Primary Examiner* — Joseph Dietrich
(74) *Attorney, Agent, or Firm* — Kilpatrick, Townsend & Stockton, LLP.

(57) ABSTRACT

A method and apparatus for determining a position of an external transceiver (24) relative to an implanted transceiver (23) comprising means (30) for measuring the strength of a magnetic field proximal to the external transceiver (24) and means for determining a position of the external transceiver (24) relative to the implanted transceiver (23) from said measured magnetic field strength. Furthermore there is disclosed is a method and apparatus for determining a skin flap thickness of a recipient of a prosthesis including a transcutaneous link between the external transceiver (24) and the implanted transceiver (23). A skin-flap thickness meter is also provided.

34 Claims, 8 Drawing Sheets

MEASUREMENT OF TRANSMITTER/RECEIVER SEPARATION

CROSS-REFERENCE TO RELATED APPLICATIONS

This application claims the priority of and is a national stage application of PCT Application No. PCT/AU2003/001140, entitled, "Method and Apparatus for Measurement Of Transmitter/Receiver Separation," filed on Sep. 4, 2003, which claims the priority of Australian Patent No. 2002951217, filed on Sep. 4, 2002. The entire disclosure and contents of the above applications are hereby incorporated by reference.

FIELD OF THE INVENTION

The present invention relates to a method and apparatus for determining the position of an external transceiver relative to an implanted transceiver. The invention also relates to a method and apparatus for determining a skin flap thickness of a recipient of a prosthesis comprising a transcutaneous link provided by an external transceiver and an implanted transceiver, and to a skin-flap thickness meter.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which comprise a microphone and an amplifier for amplifying detected sounds so that acoustic information does reach the cochlea and the hair cells.

In many people who are profoundly deaf, the reason for deafness is sensorineural hearing loss, which is caused by an absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner. It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two essential components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of an RF link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

A particular problem that the present invention seeks to address is determining a distance of separation between an external transceiver and an implanted transceiver by determining the relative position of the external transceiver to the implanted transceiver. Another problem is when an external transmitter or transceiver has been displace, for example when the external transceiver has fallen away from an optimum position upon the recipient. It is particularly relevant when the recipient, such as an infant, is unable to or unlikely to indicate such an occurrence and therefore cannot derive maximum hearing benefit from the implant system. Embodiments of the present invention may be particularly advantageous, as the distance between the transceivers impacts upon the amount of power that can be delivered to the implanted transceiver, and hence impacts upon a power source current and useful life, for instance where the power source is a battery. As such embodiments of the present invention enable a determination of the distance to be made, transmission and stimulation parameters of transmissions between the transceivers may be optimised to allow for the actual distance of separation. Optimising such parameters for the actual distance of separation leads to improved performance of the implant system, and also improves battery lifetime.

Embodiments of the present invention are particularly advantageous in that an actual field between the transmitter and receiver is measured. While an alternative prior art approach is to monitor a voltage standing wave ratio (VSWR) on the cable leading to the transmitter, such an approach requires an assumption that a change in the VSWR stems from an alteration in the link between the transmitter and receiver, whereas in fact such alterations in the VSWR may equally arise from a break in the cable or transmitter coil causing an open circuit or other such fault.

Furthermore, for the reasons given hereinbefore, the invention also seeks to provide an improved method of determining a skin-flap thickness of a recipient partly by determining the separation between the external transceiver and the implanted transceiver or stimulator/receiver. Prior art attempts at determining the separation have used battery current whereby the battery current is mapped to transceiver separation. However, measurement and monitoring of battery current may not change monotonically with varying transceiver separation, and therefore does not enable a one-to-one mapping of battery current to the separation. Conversely, measuring magnetic field strength, as with the present invention, provides a monotonic variation with transceiver separation and therefore provides a one-to-one mapping of magnetic field strength to transceiver separation.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of each claim of this application.

SUMMARY OF THE INVENTION

According to a first aspect of the invention there is provided a method of determining a position of an external transceiver relative to an implanted transceiver, the method comprising the steps of:

measuring the strength of a magnetic field proximal to the external transceiver; and determining a position of the external transceiver relative to the implanted transceiver from said measured magnetic field strength.

According to a second aspect of the invention there is provided apparatus for determining a position of an external transceiver relative to an implanted transceiver, the apparatus comprising:

means for measuring the strength of a magnetic field proximal to the external transceiver; and means for determining a position of the external transceiver relative to the implanted transceiver from said measured magnetic field strength.

It has been realised that the magnetic field strength between two transceivers preferably forming a transcutaneous link is a particularly useful factor in determining the relative positioning of the transceivers. In particular, the magnetic field strength changes monotonically with varying transceiver separation, thus allowing a one-to-one mapping of magnetic field strength to transceiver separation. However, other factors, such as battery current, may not change monotonically with varying transceiver separation, and thus do not enable a one-to-one mapping of battery current to transceiver separation, making it impossible to determine transceiver separation by monitoring or measuring such a factor.

Further, a measurement of magnetic field strength can be performed with very little power consumption, and with very little loading effect on the transmissions between the external and implanted transceivers, thus providing the advantages of simple low current implementation.

The position of the external transceiver relative to the implanted transceiver may be determined simply in order to indicate whether the external transmitter has been displaced, for example where the external transceiver has fallen away from a proper position upon the recipient. Such embodiments of the present invention are particularly useful where the recipient is unlikely to indicate such an occurrence, for instance where the recipient is an infant.

In such embodiments of the first aspect of the present invention, the step of determining preferably further comprises a step of comparing a measured strength of magnetic field proximal to the external transceiver to a threshold value; and the method of the first aspect of the invention preferably further comprises the step of indicating that the external transceiver has been displaced when the measured strength of magnetic field proximal to the external transceiver exceeds the threshold value. The step of indicating may comprise providing an audible indication such as an alarm, a visible indication or other indication.

Similarly, in such embodiments of the apparatus of the second aspect of the invention, the apparatus preferably further comprises means for comparing a measured strength of magnetic field proximal to the external transceiver to a threshold value; and means for indicating that the external transceiver has been displaced when the measured strength of magnetic field proximal to the external transceiver exceeds the threshold value. The means for indicating may comprise an audible alarm, a visible indicator, or other type of indicator.

Alternatively, the position of the external transceiver relative to the implanted transceiver may be determined in order to estimate a distance of separation between the external transceiver and the implanted transceiver. Such embodiments of the invention may be particularly advantageous, as the distance between the transceivers impacts upon the amount of power that can be delivered to the implanted transceiver, and hence impacts upon a power source current and useful life, for instance where the power source is a battery. As such embodiments of the present invention enable a determination of the distance to be made, transmission and stimulation parameters of transmissions between the transceivers may be optimised to allow for the actual distance of separation. Optimising such parameters for the actual distance of separation leads to improved performance of the implant system, and also improves battery lifetime.

In such embodiments of the first aspect of the invention, the step of determining preferably further comprises mapping a measured value of magnetic field strength proximal to the external transceiver to a distance value. The step of mapping may comprise consulting a look-up table comprising a plurality of pairs of values, each pair of values mapping a particular magnetic field strength to a corresponding transceiver separation distance.

Alternatively the step of mapping may comprise algorithmically converting said measured value of magnetic field into a corresponding transceiver separation distance.

Similarly, in such embodiments of the second aspect of the invention, the apparatus preferably further comprises means for mapping a measured value of magnetic field strength proximal to the external transceiver to a distance value. The means for mapping may comprise a look-up table comprising a plurality of pairs of values of magnetic field strength to transceiver separation distance.

Alternatively the means for mapping may comprise means for algorithmically converting said measured value of magnetic field into a corresponding transceiver separation distance.

According to a third aspect of the invention there is provided a method of determining a skin flap thickness of a recipient of a prosthesis comprising a transcutaneous link provided by an external transceiver and an implanted transceiver, the method comprising the steps of:

measuring a strength of a magnetic field proximal to the external transceiver when the external transceiver is positioned so as to implement the transcutaneous link; and determining a skin flap thickness of the recipient by determining a position of the external transceiver relative to the implanted receiver from said measured magnetic field strength.

According to a fourth aspect of the invention there is provided apparatus for determining a skin flap thickness of a recipient of a prosthesis comprising a transcutaneous link provided by an external transceiver and an implanted transceiver, the apparatus comprising:

means for measuring a strength of a magnetic field proximal to the external transceiver when the external transceiver is positioned so as to implement the transcutaneous link; and means for determining a skin flap thickness of the recipient by determining a position of the external transceiver relative to the implanted receiver from said measured magnetic field strength.

A transcutaneous link formed by the external transceiver and the implanted transceiver may comprise an RF link. The transcutaneous link may be unidirectional, in that the external transceiver comprises a transmitter, and the implanted transceiver comprises a receiver. Alternatively, it is envisaged that the transcutaneous link may be bidirectional, in that both the external transceiver and the implanted transceiver may transmit and receive signals across the transcutaneous link. In particular, it is envisioned that the external transceiver will be operable to transmit both data and power across the transcutaneous link, and to receive data across the transcutaneous link. Similarly, it is envisioned that the implanted transceiver will be operable to receive both power and data across the transcutaneous link and to transmit data across the transcutaneous link.

The means for measuring the strength of the magnetic field proximal to the external transceiver may comprise a pickup coil positioned proximal to the external transceiver. Preferably, the pickup coil is positioned in a plane substantially perpendicular to a primary axis of the magnetic field produced by the transceivers. The pickup coil may comprise an open circuited single turn, positioned concentrically with turns of the external transceiver. In such embodiments, a voltage induced on the pickup coil will be indicative of a magnetic field proximal to the external transceiver, and may thus be used in determining a position of the external transceiver relative to the implanted transceiver.

The external transceiver will typically be capable of transmitting power and data to the implanted transceiver. However, the external transceiver is preferably capable of receiving data from the implanted transceiver. Similarly, the implanted transceiver will typically be capable of receiving power and data from the external transceiver, but is preferably also capable of transmitting data to the external transceiver.

It is to be appreciated that measurement of the magnetic field strength proximal to the implanted transceiver may similarly yield information regarding the position of the external transceiver relative to the implanted transceiver and is thus within the scope of the present invention. However it is unlikely that such internal field measurements will be efficient due to the limited power available to an implanted portion of a prosthesis, and the difficulty of processing and communicating such measurements from the implanted portion to the external transceiver.

According to a fifth aspect of the invention there is provided a skin-flap thickness meter, the meter comprising:

a meter transmitter coil for placement proximal to an implanted transceiver such that the meter transmitter coil and the implanted transceiver coil are separated by substantially the skin-flap thickness;

means for measuring a strength of a magnetic field proximal to the meter transmitter coil when the meter transmitter coil is placed proximal to the implanted transceiver; and means for determining a skin flap thickness by determining a position of the meter transmitter coil relative to the implanted transceiver from said measured magnetic field strength.

According to a sixth aspect of the invention there is provided apparatus for determining a position of an external transceiver relative to an implanted transceiver, the apparatus comprising:

means for measuring the strength of a magnetic field proximal to the external transceiver;

means for determining a position of the external transceiver relative to the implanted transceiver from said measured magnetic field strength;

means for comparing a measured strength of magnetic field proximal to the external transceiver to a threshold value;

means for indicating that the external transceiver has been displaced when the measured strength of magnetic field proximal to the external transceiver exceeds the threshold value; and means for mapping comprises a look-up table comprising a plurality of pairs of values of magnetic field strength to transceiver separation distance.

According to a seventh aspect of the invention there is provided apparatus for determining a skin flap thickness of a recipient of a prosthesis comprising a transcutaneous link provided by an external transceiver and an implanted transceiver, the apparatus comprising:

a pick-up coil for measuring a strength of a magnetic field proximal to the external transceiver when the external transceiver is positioned so as to implement the transcutaneous link, the pickup coil being positioned in a plane substantially perpendicular to a primary axis of the magnetic field produced by the transceivers;

wherein a voltage induced on the pickup coil is indicative of a magnetic field proximal to the external transceiver; and means for determining a skin flap thickness of the recipient by determining a position of the external transceiver relative to the implanted receiver from said measured magnetic field strength.

BRIEF DESCRIPTION OF THE DRAWINGS

Preferred embodiments of the invention will hereinafter be described, by way of example only, with reference to the accompanying drawings in which.

DETAILED DESCRIPTION OF THE PREFERRED EMBODIMENTS

Figure 1:
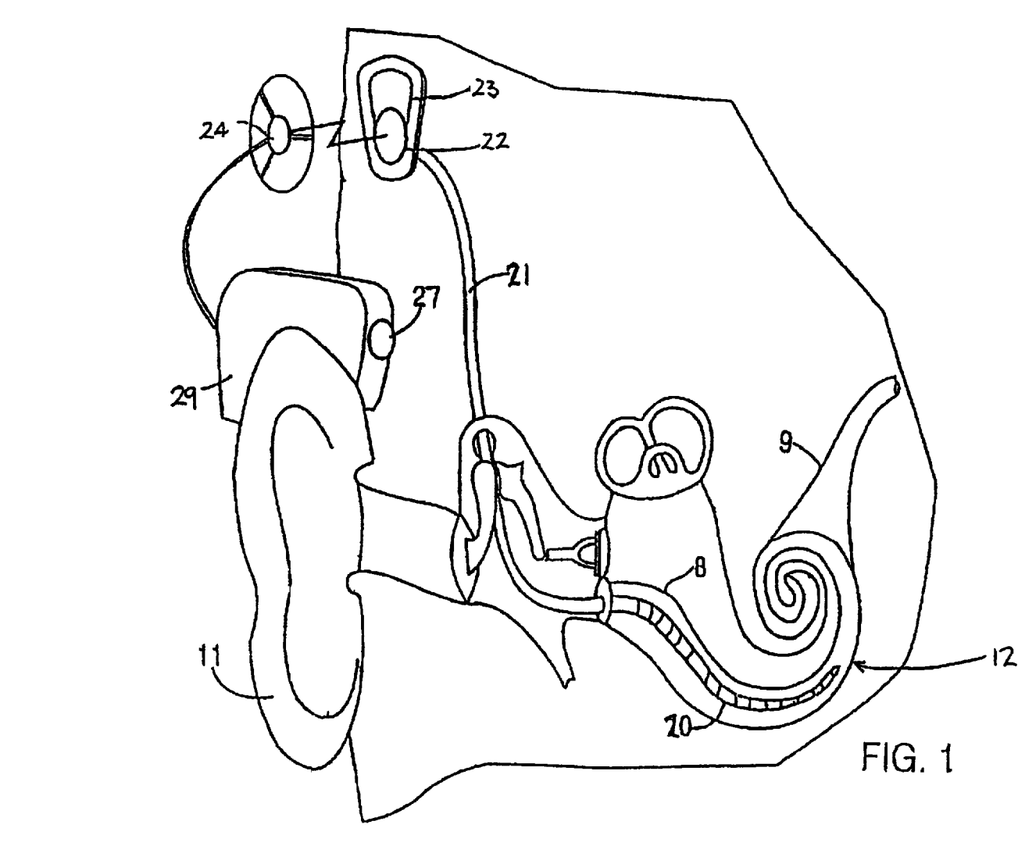
FIG. 1 is a pictorial representation of a cochlear implant system within which the present invention may be implemented.

While the present invention is not directed solely to a cochlear implant, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn elsewhere on the recipient's body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930. As depicted diagrammatically in FIG. 1, the cochlear implant electrode array 20 has traditionally been inserted into the initial portion of the scala tympani of the cochlea 12 up to about a full turn within the cochlea.

A sound processor (not shown) of the external component 29 includes an amplifier and a speech processor that uses a coding strategy to extract speech from the sounds detected by the microphone 27. In the depicted embodiment, the speech processor of the cochlear implant can perform an audio spectral analysis of the acoustic signals and output channel amplitude levels. The sound processor can also sort the outputs in order of magnitude, or flag the spectral maxima as used in the SPEAK strategy developed by Cochlear Ltd. Other coding strategies could be employed.

Figure 2:
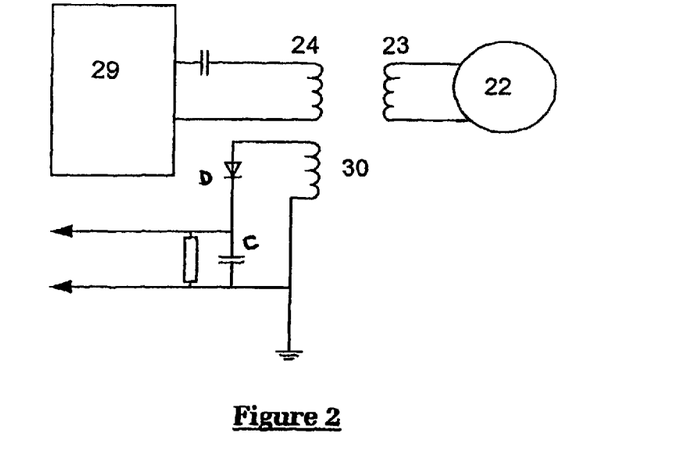
FIG. 2 is a circuit diagram illustrating implementation of an embodiment of the present invention.

FIG. 2 is a circuit diagram illustrating implementation of an embodiment of the present invention in a cochlear implant system of the type shown in FIG. 1. The speech processor of the external component 29 drives the transmitter coil 24, which transmits power and data to receiver coil 23, for the implanted stimulator unit 22. In accordance with the present invention, a pickup coil 30 is provided for detecting the strength of a magnetic field proximal to the transmitter 24. The pickup coil 30 is positioned in a plane substantially perpendicular to a primary axis of the magnetic field produced by the transmitter coil 24 and receiver coil 23. The pickup coil comprises an open circuited single turn, positioned concentrically with turns of the transmitter coil 24. A voltage is induced on the pickup coil which is indicative of a magnetic field strength proximal to the transmitter coil 24. The output of the pickup coil 30 is passed through a peak detector comprising diode D and capacitor C.

In the present embodiment, the RF link of the implant system operates at a signal frequency of 5 MHz. The transmitter coil 24 and receiver coil 23 are stagger-tuned to achieve the bandwidth needed for a 100% amplitude modulated RF signal. The transmitter resonance circuit 24 is usually tuned below the signal frequency, while the implant receiver circuit 23 is tuned slightly above the signal frequency. As a result, the effective impedance seen by the RF drivers of the speech processor of the external component 29, at the signal frequency, is inductive. This inductive impedance increases when the coupling between the coils 23, 24 is increased, by reducing the distance between the coils 23, 24. As a result, the current through the transmitter coil 24, and the magnetic field in the vicinity of the coil 24, falls when the distance between the coils is reduced.

This phenomena can also be explained in terms of the interaction between the magnetic fields surrounding the transmitter coil 24 and receiver coil 23. The magnetic field generated by the receiver coil 23 is a secondary field that opposes the primary field of the transmitter coil 24. The interaction between the two opposite fields reduces the effective field near the transmitter coil 24. This effect is increased as the distance between the coils 23, 24 is reduced.

The invention is based on measuring the strength of the magnetic field in the vicinity of the transmitter coil 24. As this field increases monotonically with the distance between the transmitter coil 24 and receiver coil 23, the measured field strength can be calibrated to estimate the distance between the coils 23, 24, and also to indicate if that distance exceeds a preset value, for example if the coil has fallen off the user's head.

However, other factors, such as battery current, may not change monotonically with varying transceiver separation, and thus do not enable a one-to-one mapping of battery current to transceiver separation, making it impossible to determine transceiver separation by monitoring or measuring such a factor.

Further, a measurement of magnetic field strength can be performed with very little power consumption, and with very little loading effect on the transmissions between the external and implanted transceivers, thus providing the advantages of simple low current implementation.

The circuit shown in FIG. 2 was simulated using OrCad Pspice version 9.2. The simulation model included circuit models for the CI24M implant produced by Cochlear Ltd, ESPrit 3G speech processor produced by Cochlear Ltd and a single turn pickup coil.

A simplified spice model was used for both the implant and the speech processor. The ESPrit 3G model included the major variable that affects and/or sets the battery current, output RF current, stimulation phase width, and intra-frame gap, as well as the RF-data mark-space ratio. The implant model, on the other hand, included all the power consuming components such as the antenna resistance, transformer losses, diode, IC consumption and stimulation current. The coupling coefficient, k, between the transmitter and receiver coils was expressed as a function of the distance d between the coils:

$$k = \frac{1.26}{2.6 + d},$$

where d is in mm.

This value of k was empirically obtained from the particular antennae used in the circuit depicted in FIG. 2. The peak detector decay time constant was set to 10 ms. This time constant was chosen much longer than the stimulation period of the SPEAK strategy, set to 2000 pps in the Spice model.

The circuit was simulated using stimulation rates from 2000 pps to 13900 pps, stimulation current ranging from 0 to 1.8 mA and link range from 1 to 20 mm. The circuit parameters shown in the following table were used to study the effect of the distance between the coils.

| Parameter | Value |
| --- | --- |
| Vbatt | 3.0 V |
| Stim rate | 13.9 kHz |
| Phase width | 25 us |
| Stim current | 1 mA |
| Transmitter coil tuned freq | 4.8 MHz |
| Receiver coil tuned freq | 5.25 MHz |

-continued

| Parameter | Value |
|---|---|
| Pickup inductance | 60 nH |
| Coupling coefficient of pickup coil | 0.7 |

Figure 3:
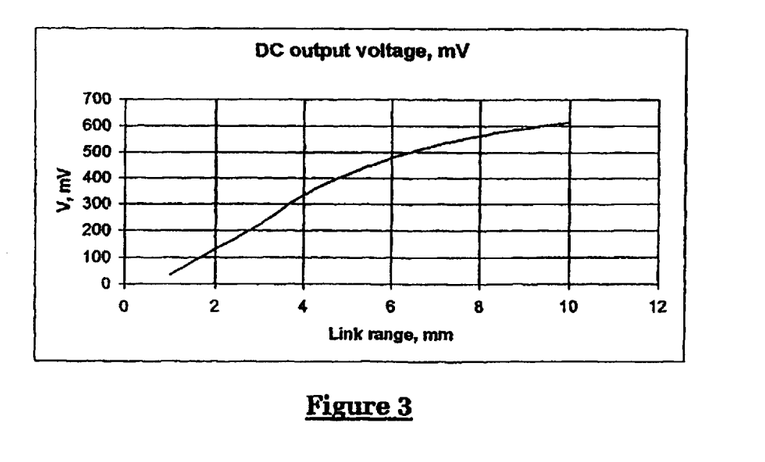
FIG. 3 depicts variation of magnetic field strength with transceiver separation for the embodiment of FIG. 2.
Figure 4:
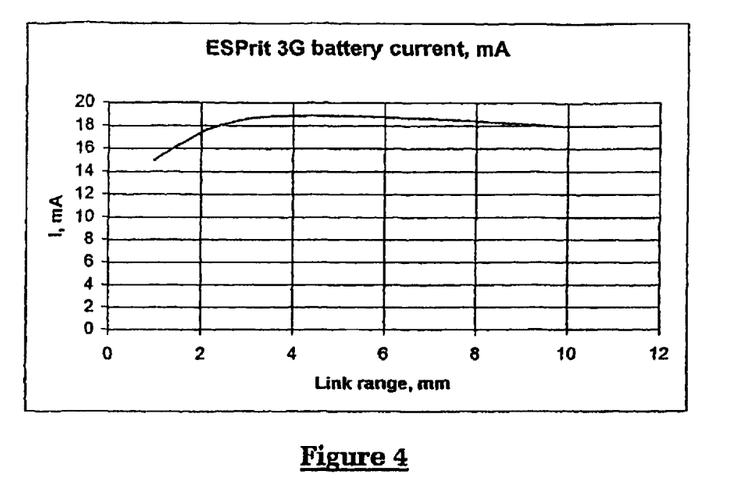
FIG. 4 depicts variation of battery current with transceiver separation for the embodiment of FIG. 2.

The simulation results are shown in FIG. 3 and FIG. 4. FIG. 3 depicts the peak detector output voltage versus link range (transmitter 24/receiver 23 separation). This output voltage depends on the strength of the magnetic field, normal to the pickup coil 30. In this example, the pickup coil 30 is a single track printed on a PCB upon which the transmitter coil 24 is also printed. The coupling coefficient between the transmitter 24 and pickup coil 30 is assumed to be 0.7. Higher coupling can be achieved in practice by the careful placement of the pickup coil 30 relative to the transmitter 24. Higher output signals can also be obtained if a two-turn (or more) pickup coil is used.

FIG. 3 reveals that the magnetic field of the transmitter 24 increases with the distance between the transmitter coil 24 and receiver coil 23 (link range). When that distance exceeds 20 mm, the output voltage reaches about 780 mV (not shown in the figure). FIG. 3 also reveals that the increase in magnetic field is monotonic as the link range increases from 1 mm to 10 mm.

FIG. 4 depicts the battery current, which reaches a peak value of 18.9 mA at 4 mm then gradually drops to 18 mA at 10 mm, and to 17 mA at 20 mm (not shown in the figure). Thus, the battery current does not vary monotonically with increasing link range between the transmitter 24 and receiver 23.

FIGS. 3 and 4 clearly show that the battery current cannot be used to estimate the link range, as a given value of battery current can not be equated to a single value of transceiver separation. On the other hand, there is a one to one correlation between the output voltage of the peak detector C, D and the distance between the transmitter coil 24 and receiver coil 23.

It is to be noted that the battery current is proportional to the total system power. On the other hand, the strength of the magnetic field in the vicinity of the transmitter coil 24 is proportional to the stored reactive energy. The relationship between the active and reactive energy components depends on the phase angle of the coil current relative to the driving voltage. It is this phase angle which changes with the coupling coefficient between the transmitter coil 24 and receiver coil 23.

The peak detector output depends slightly on the implant power, as explained below with respect to FIGS. 5 to 10. The effect of the implant power on the output of the peak detector becomes negligible at maximum link range.

As the distance between the coils 23, 24 is gradually increased from minimum to maximum link range, a number of effects occur. Firstly, the power delivered to the implant 22 is reduced. Secondly, transmitter losses increase due to increased RF current.

These changes determine the behavior of the battery current, whereas the current through the transmitter coils 23, 24, and hence the magnetic field strength, increases monotonically towards an asymptotic value.

The peak magnetic field, normal to the pickup coil 30, depends on the sum of the electric fields produced by the transmitter coil 24 and receiver coil 23. The peak magnetic field depends slightly on the stimulation parameters, namely the stimulation current and the stimulation rate. The influence of the stimulation parameters is relatively small because the stimulation power represents a small part of the total system power which includes the implant 22 and transmitter coil 24 losses, as follows:

Total transmitter coil power=transmitter coil losses+ implant losses+stimulation power On the other hand, the ratio of the stored to dissipated energy is the effective quality factor of the loaded transmitter coil, as follows:

$Q$=stored energy per cycle/dissipated energy per cycle=reactive power/dissipated power But $Q \gg 1$, therefore Reactive power$\gg$dissipated power, which yields:

Reactive power$\gg$transmitter coil losses+implant losses+stimulation power

That is, Reactive power$\gg$Stimulation power.

The magnetic field is proportional to the reactive power, which is much higher than the stimulation power. Therefore, the stimulation parameters can only have a second order effect on the peak amplitude of the magnetic field. This is in agreement with the simulation results.

The stimulation rate, however, has a stronger effect due to the fact that the peak detector used in FIG. 2 is not ideal and has a finite decay time constant.

The significance of the above discussion is to highlight the fact that, at long link range, the peak detector output is not sensitive to the stimulation current, but is affected by the stimulation rate. This effect must be taken into account when the peak detector output is used to estimate the distance between the coils.

One application of the present invention is in estimating a skin flap thickness of a recipient of a cochlear implant system of the type shown in FIG. 1, that is, the thickness of skin between the implanted receiver coil 23 and the external transmitter coil 24.

To date, estimating the skin flap thickness has been done in a clinic where the speech processor is powered from the programming system. In this case, specific stimulation parameters are used in order to achieve consistent and repeatable skin flap thickness estimates.

However, the circuit of FIG. 2 can be used to estimate the skin flap thickness. A first method by which the skin flap thickness may be estimated by using the circuit of FIG. 2, involves using the recipient's own speech processor to create the RF magnetic field. This method requires providing a signal path from the peak detector output to the programming system. In this case, the transmitter coil is excited with maximum frame rate at a regulated supply voltage supplied by the programming system. This eliminates the dependency of the peak detector output on the stimulation rate and supply voltage. A look up table stored in the programming system can be used to map the measured voltage to skin flap thickness.

A second method by which the skin flap thickness may be estimated by using the circuit of FIG. 2, involves using a stand-alone device with built-in oscillator and voltage measurement circuit. In this second method, the stand-alone device is essentially a skin flap thickness meter. The meter contains a 5 MHz crystal oscillator with low output impedance drivers to drive a tuned transmitter coil with continuous 5 MHz square voltage. The transmitter coil contains a pickup coil and a peak detector similar to that shown in FIG. 2. The DC output of the peak detector is measured using a built-in analog to digital converter (ADC). The output of the ADC is converted to skin flap thickness, which is then displayed by the meter.

Another application of the present invention is in detecting displacement of the external transmitter 24 from the user's head, for example where the transmitter coil 24 falls off an infant's head. Such coil-off detection is based on detecting a link range greater than a set threshold value, which would typically be set to around 10-12 mm. Such a circuit solution has to be implemented on the transmitter coil and/or the speech processor. For reliable detection, the circuit has a low sensitivity to battery voltage, stimulation current, stimulation rate, ambient temperature and implant tuning. The circuit also operates without requiring precision measurement of the output voltage of the peak detector. The circuit solution is simple, uses a small number of components and has low current consumption.

One manner in which many or all of the above requirements may be met is by comparing the peak detector signal with another reference signal, which has all of the major characteristics of the peak detector signal except its dependency on the coil separation. The reference signal should be generated from a peak detector similar to that shown in FIG. 2 in order to have the same decay time constant, voltage offsets and temperature characteristics as the measured signal, and should be proportional to the battery voltage to track the changes of the measured signal with the battery voltage. Further, the reference signal should vary with the stimulation rate in a manner similar to that of the measured signal, and should have low sensitivity to the implant power, especially at relatively large link ranges.

Figure 5:
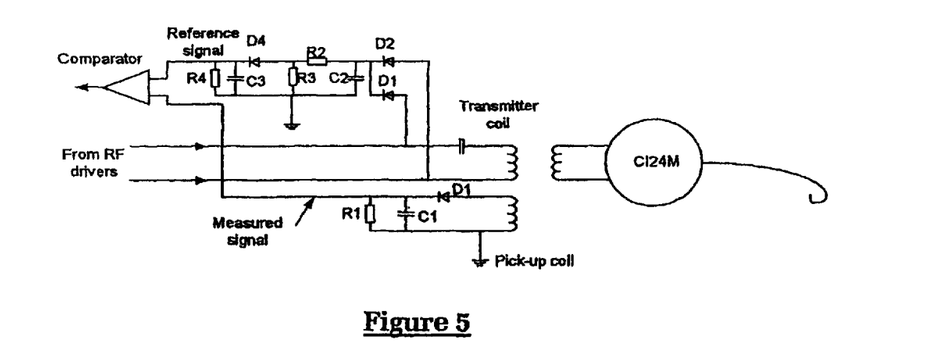
FIG. 5 is a circuit diagram illustrating a coil-off detection circuit in accordance with the present invention.

A simple manner in which the reference signal can be obtained comprises rectifying and peak-detecting the output of the RF drivers of the speech processor, as shown in FIG. 5. In FIG. 5, the output of the speech processor, in this instance an ESPrit 3G speech processor of the type produced by Cochlear Ltd, is full-wave rectified by $D_1$ and $D_2$. The DC voltage across $C_2$ tracks the amplitude of the ESPrit 3G RF output voltage. This DC voltage can be made to vary with the stimulation rate in a manner which is similar to that of the voltage across $R_1$. This is determined by the time constant:

$$\tau_1 = C_2 \cdot (R_2 + R_3)$$

When this time constant is made very small, the voltage across $C_2$ will strongly depend on the stimulation rate, and vice versa.

The voltage divider ratio $R_3/(R_2+R_3)$ is designed such that the voltage across $R_3$ is substantially equal to the peak voltage across $R_1$ at the designated threshold for the maximum link range. The voltage across $R_3$ is applied to a diode-capacitor ($D_4, C_3$) peak detector similar to that used with the pickup coil 30. This is to match the time variation and the temperature characteristics of the measured signal and the reference signal.

A voltage comparator is used to compare the measured and reference signals. The output of the comparator can be used to trigger an audible alarm to alert the carers if the transmitter coil is removed.

The way the circuit operates is based on matching the amplitudes of the measured and reference signals at the maximum link range. Below that range, the measured signal is smaller and the output of the comparator is disasserted. However, if the separation between the transmitter coil 24 and receiver coil 23 exceeds the maximum link range, the measured signal exceeds the reference signal and triggers the comparator.

The recommended component values for typical circuit conditions of the ESPrit 3G are given below.

D1 to D4: low cut-in voltage high-speed diodes
R1=R4=1 MΩ
R2=220 kΩ
R3≅100 kΩ
C1=C3=10 nF
C2=100 pF
Pickup coil: printed single turn on the transmitter coil PCB. A single turn from an electrostatic shield can be used.

Where the transmitter coil is implemented on a printed circuit board, the circuit of FIG. 5 can be fully integrated on the PCB of the transmitter coil. The comparator can be replaced with a low voltage-low power low speed operational amplifier. The DC power for the comparator/amplifier can be provided from the RF drivers' signal using a voltage doubler circuit to provide the amplifier with positive and negative DC supply rails. A power cost will be in overloading the RF drivers with the comparator. DC power, which can be as low as 50 uA at 3V. However, this is an insignificant cost compared with the total RF power consumed by the system. The advantage of integrating the circuit on the transmitter coil is that it reduces the number of the coil cable connectors, and substantially guarantees the matching between the circuit components especially with respect to changes with temperature.

Figure 6:
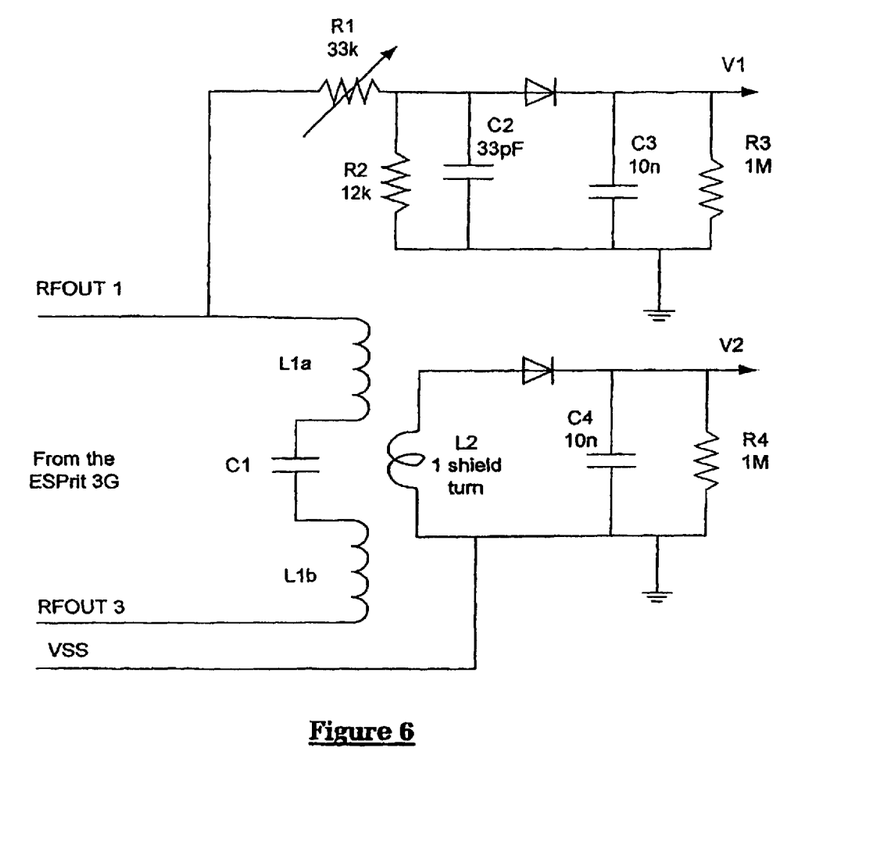
FIG. 6 is a circuit diagram of a circuit used for verification of coil-off detection.

FIG. 6 is a circuit diagram of a circuit used for verification of coil-off detection, for use with an ESPrit 3G speech processor. The circuit of FIG. 6 was used to investigate and verify the concept and to study the sensitivity to different circuit and stimulation parameters. The prototype was measured in a laboratory with both SPEAK and 14.2 kHz stimulation, at both quiet and loud sound environments, and at different battery voltages.

The circuit is designed for minimum loading on the RF drivers of the ESPrit 3G. It uses a small number of components which can be all mounted on the transmitter coil printed circuit board. The transmitter coil has 3 open tracks on each side used for electrostatic shielding. One shield track (nearly a full turn) is used as the pickup coil.

$R_1$, $R_2$ and $C_2$ form a potential divider and a low pass filter for the RF signal on RFOUT 1. The filter parameters are chosen such that the peak voltage across $C_2$ varies with the pulse width of the RF signal. This allows the output V1 to track the RF power level at different battery voltages. In FIG. 6 $R_1$ is a variable resistor to facilitate accurate adjustment for the best detection thresholds. In a non-testing circuit, it is expected that $R_1$ will be replaced with a fixed resistor.

The voltage across $C_{10}$ and the voltage across the pickup coil $L_2$ are peak detected using identical envelope detectors. The DC output V1 is the coil-off detection voltage threshold. V2 is the coil-off signal. The voltage V2 increases as the separation between the transmitter coil and the implanted receiver coil increases. At or above the coil-off detection distance, V2 exceeds V1.

The measurement method was as follows. The ESPrit 3G was loaded with 2 patient maps. The first was a 14.2 kpps map while the second was a SPEAK 2 kpps map. A "quiet" sound condition was simulated by removing the microphone and replacing it with a 1 kΩ resistor. A "loud" sound condition was simulated by placing a loud radio close to the microphone. The voltages V1 and V2 were measured under the conditions shown in table 1 below.

Each of the following tests was carried out at room temperature. A total of 40 tests (table 1) were carried out. During each test the distance was varied from 0 to 14 mm in 2 mm steps, after which the distance was set to more than 10 cm (simulating very large distance). These 40 tests cover the different circuit parameters, in order to demonstrate the sensitivity of the coil-detection method to these parameters.

At each distance, the test was repeated 4 times; at stimulation rates of 2000 pps and 14400 pps, and in both "quiet" and "loud" sound environments. The measurements were also repeated at different implant tuning frequencies of 5.1 MHz, 5.25 MHz and 5.4 MHz, and at different supply voltages of 2.7V, 3.0V and 3.3V.

To check the sensitivity to the transmitter coil tuning the test was repeated for implant tuning of 5.25 MHz and power supply voltage of 3V. The transmitter coil was tuned to its minimum limit and then to its maximum limit of 4.725 MHz and 4.775 MHz respectively.

TABLE 1

Test Conditions

| Test Number | Transmitter Coil Tuning Frequency | Implant Coil Tuning Frequency | VDD | Stimulation Rate | Sound level |
|---|---|---|---|---|---|
| 1 | 4.775 MHz | 5.1 MHz | 2.7 V | 2000 pps | Quiet |
| 2 | | | | | Loud |
| 3 | | | | 14200 pps | Quiet |
| 4 | | | | | Loud |
| 5 | | | 3.0 V | 2000 pps | Quiet |
| 6 | | | | | Loud |
| 7 | | | | 14200 pps | Quiet |
| 8 | | | | | Loud |
| 9 | | | 3.3 V | 2000 pps | Quiet |
| 10 | | | | | Loud |
| 11 | | | | 14200 pps | Quiet |
| 12 | | | | | Loud |
| 13 | | 5.25 MHz | 2.7 V | 2000 pps | Quiet |
| 14 | | | | | Loud |
| 15 | | | | 14200 pps | Quiet |
| 16 | | | | | Loud |
| 17 | | | 3.0 V | 2000 pps | Quiet |
| 18 | | | | | Loud |
| 19 | | | | 14200 pps | Quiet |
| 20 | | | | | Loud |
| 21 | | | 3.3 V | 2000 pps | Quiet |
| 22 | | | | | Loud |
| 23 | | | | 14200 pps | Quiet |
| 24 | | | | | Loud |
| 25 | | 5.4 MHz | 2.7 V | 2000 pps | Quiet |
| 26 | | | | | Loud |
| 27 | | | | 14200 pps | Quiet |
| 28 | | | | | Loud |
| 29 | | | 3.0 V | 2000 pps | Quiet |
| 30 | | | | | Loud |
| 31 | | | | 14200 pps | Quiet |
| 32 | | | | | Loud |
| 33 | | | 3.3 V | 2000 pps | Quiet |
| 34 | | | | | Loud |
| 35 | | | | 14200 pps | Quiet |
| 36 | | | | | Loud |
| 37 | 4.725 MHz | 5.25 MHz | 3.0 V | 2000 pps | Quiet |
| 38 | | | | | Loud |
| 39 | | | | 14200 pps | Quiet |
| 40 | | | | | Loud |

The test results are set out towards the end of the present specification. The distances at which the measured signal (V2) exceeds the threshold voltage (V1) are highlighted in the results tables. Because the measurements were done at increments of 2 mm, the highlighted points could be equal to or exceed the correct detection point by up to 2 mm.

Figure 7:
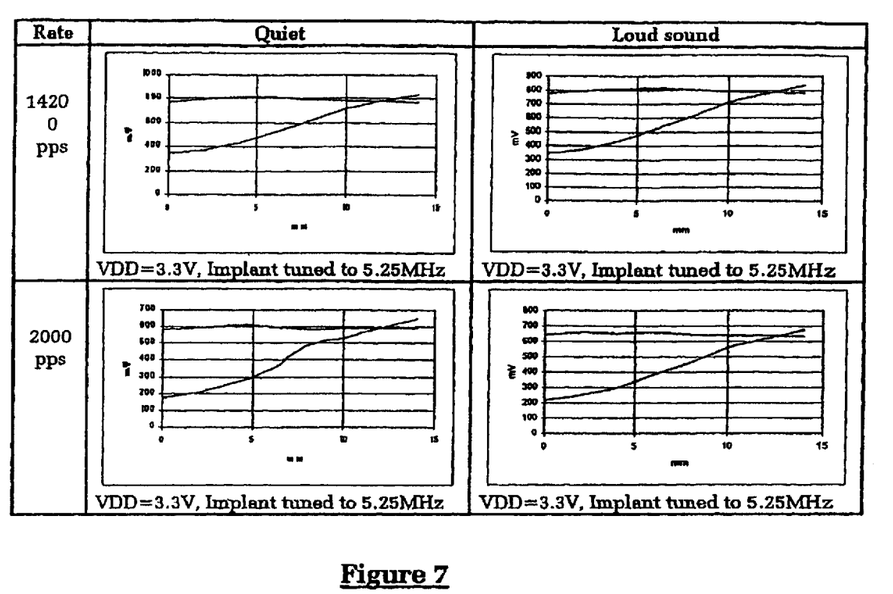
FIG. 7 illustrates the variation of magnetic field with transceiver separation for particular values of stimulation rate and sound level for the circuit of FIG. 6.

FIG. 7 illustrates the reference and measured voltages, V1 and V2 respectively, at 14.2 kpps and 2 kpps in quiet and loud sound environments. The battery voltage was set to 3.3V. The implanted coil was tuned to its nominal frequency of 5.25 MHz. FIG. 7 shows that the reference voltage is automatically adjusted to a threshold distance of between 12 and 13 mm. Above this threshold, an alarm will be triggered to indicate a coil-off condition.

Figure 8:
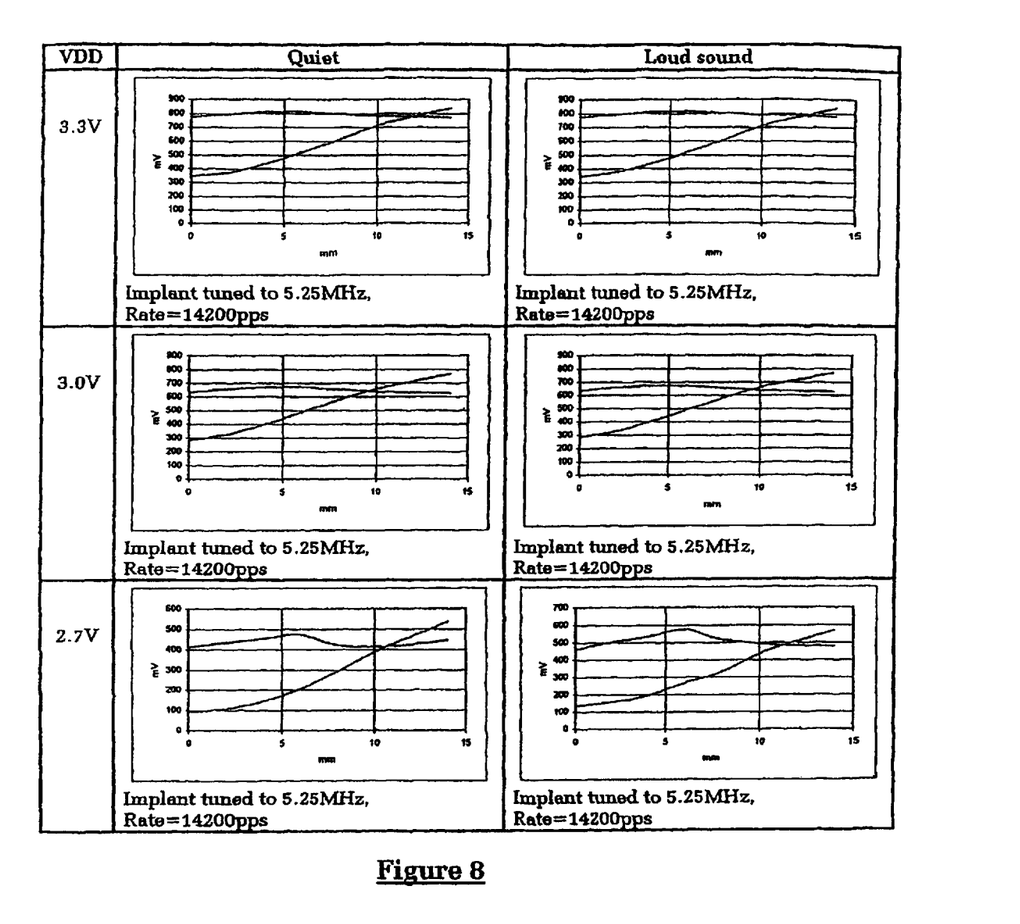
FIG. 8 illustrates the variation of magnetic field with transceiver separation for particular values of supply voltage and sound level for the circuit of FIG. 6.

FIG. 8 depicts the reference and measured voltages, V1 and V2 respectively, at 14.2 kpps in quiet and loud sound environments, and at supply voltages of 3.3, 3.0 and 2.7V respectively. The implanted coil was tuned to its nominal frequency of 5.25 MHz. These results indicate the detection distance has low sensitivity to the supply voltage, as the point of intersection of the V1 and V2 curves varies by only small amounts.

Figure 9:
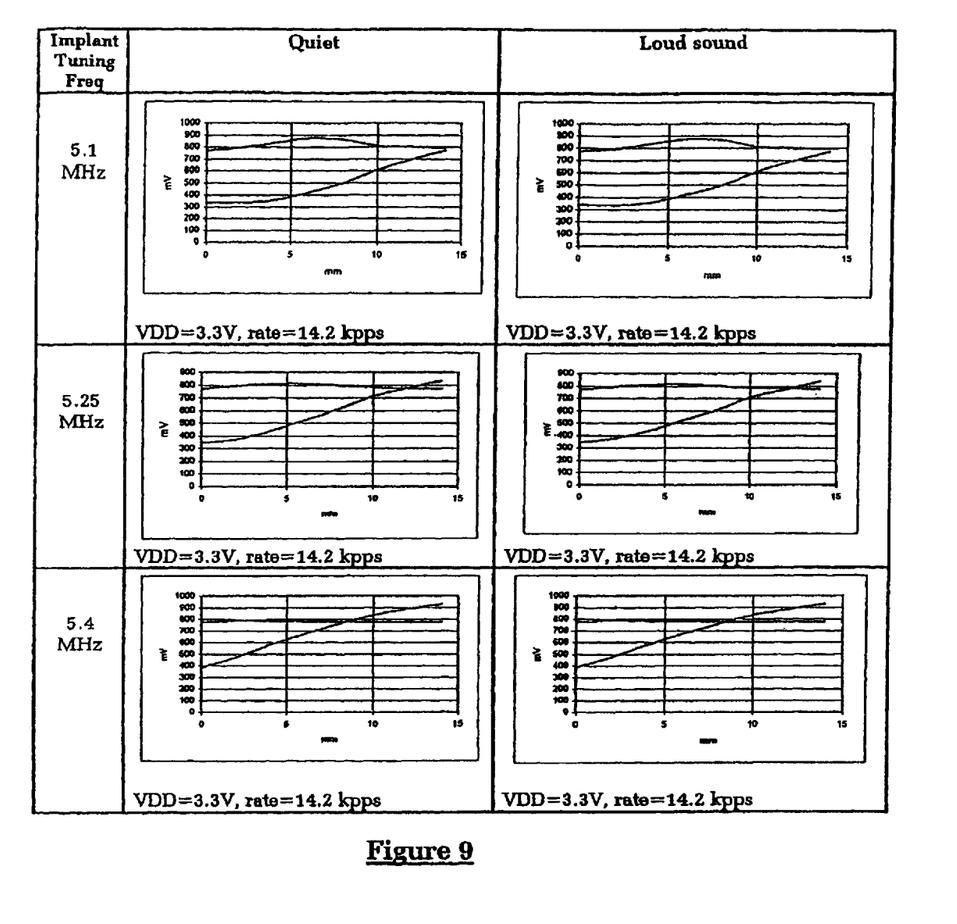
FIG. 9 illustrates the variation of magnetic field with transceiver separation for particular values of implanted coil tuning and sound level for the circuit of FIG. 6.

FIG. 9 reveals that the coil-off detection distance is reasonably sensitive to the tuning frequency of the implanted coil. When the implant is tuned to 5.4 MHz, the detection threshold distance drops to 8.5 mm. The detection distance increases as the tuning frequency of the implanted coil is reduced to 5.1 MHz. At this frequency, the circuit will detect coil removal if the distance exceeds about 14 mm.

Figure 10:
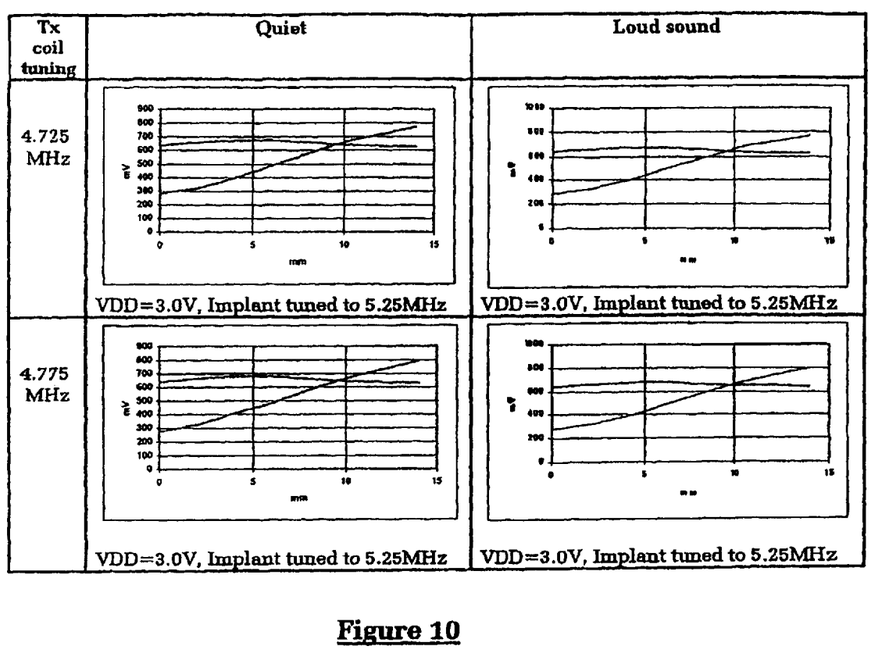
FIG. 10 illustrates the variation of magnetic field with transceiver separation for particular values of external coil tuning and sound level for the circuit of FIG. 6.

The effect of the transmitter coil tuning is shown in FIG. 10. The results, at 3V supply voltage and 14.2 kHz stimulation rate, indicate that varying the transmitter coil tuning from 4.725 MHz to 4.775 MHz has substantially no effect on the distance threshold.

SUMMARY OF RESULTS

High Rate Stimulation

| Test # | Detection Distance |
|---|---|
| 3 | 10.8 |
| 4 | 11.4 |
| 7 | 11.8 |
| 8 | 11.8 |
| 11 | 14.9 |
| 12 | 15 |
| 15 | 9.5 |
| 16 | 9.5 |
| 19 | 9.6 |
| 20 | 9.6 |
| 23 | 11.9 |
| 24 | 12.3 |
| 27 | 6.3 |
| 28 | 6.2 |
| 31 | 6.2 |
| 32 | 6.2 |
| 35 | 8.5 |
| 36 | 8.5 |

The above table shows the coil-off detection threshold distance at all combinations of supply voltage and tuning frequencies.

Low Rate Stimulation

Similar to the high rate stimulation, the lowest detection distance occurred at low battery voltage and high implant tuning frequency (tests 25, 26, 29 and 30).

| Test # | Detection Distance |
|---|---|
| 1 | 6.5 |
| 2 | 8.4 |
| 5 | 7.0 |
| 6 | 9.3 |
| 9 | 13.7 |
| 10 | 13.9 |
| 13 | 6.7 |
| 14 | 7.9 |
| 17 | 6.9 |
| 18 | 8.8 |
| 21 | 12 |

-continued

| Test # | Detection Distance |
|---|---|
| 22 | 12.7 |
| 25 | 5.3 |
| 26 | 5.6 |
| 29 | 5.5 |
| 30 | 6.0 |
| 33 | 9.1 |
| 34 | 9.2 |

The measurement results discussed above show the usefulness of the coil-off detection circuit embodiment of the present invention. The method discussed has low sensitivity to most of the circuit parameters and variables, except for the implant tuning if at the upper end of the tuning range. This problem can be easily solved by adding a small DC offset to the reference voltage V1. By adjusting the value of that offset a detection distance in the range 8 mm to 15 mm can be achieved for all circuit conditions.

While an embodiment of the invention has been discussed in which a threshold detection of a coil-off condition is performed, it is to be appreciated that alternative embodiments of the present invention may be used to estimate an actual distance between implanted and external coils. For example, a look-up table may be experimentally derived from a voltage to distance calibration measurement, such as the voltage measurements revealed in FIGS. 7 to 10. Such a look-up table may then be used in converting measured magnetic field strengths to estimated transceiver separation values. Alternatively, a best-fit algorithm may be derived from the measured voltage/distance values, for use in converting measured magnetic field strengths to estimated transceiver separation values.

APPENDIX

Test Results

| | Test 1 2.0 kHz Quiet | | Test 2 2.0 kHz Loud | | Test 3 14.2 kHz Quiet | | Test 4 14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 254 | 29 | 306 | 46 | 412 | 93 | 463 | 136 |
| 2 | 258 | 42 | 323 | 65 | 435 | 108 | 502 | 157 |
| 4 | 248 | 90 | 341 | 107 | 453 | 146 | 532 | 194 |
| 6 | 227 | 196 | 343 | 177 | 473 | 205 | 575 | 267 |
| 8 | 228 | 311 | 283 | 270 | 423 | 292 | 519 | 330 |
| 10 | 230 | 387 | 302 | 359 | 414 | 388 | 494 | 436 |
| 12 | 227 | 422 | 288 | 415 | 425 | 463 | 482 | 506 |
| 14 | 225 | 446 | 286 | 462 | 446 | 537 | 478 | 566 |
| >100 | 222 | 565 | 270 | 609 | 440 | 789 | 457 | 811 |

| | Test 5 2.0 kHz Quiet | | Test 6 2.0 kHz Loud | | Test 7 14.2 kHz Quiet | | Test 8 14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 323 | 56 | 405 | 93 | 634 | 262 | 635 | 263 |
| 2 | 329 | 72 | 405 | 105 | 664 | 274 | 664 | 275 |
| 4 | 318 | 129 | 419 | 155 | 706 | 316 | 707 | 318 |
| 6 | 298 | 234 | 415 | 236 | 746 | 391 | 746 | 391 |
| 8 | 297 | 367 | 400 | 339 | 732 | 477 | 733 | 479 |
| 10 | 300 | 470 | 408 | 442 | 673 | 586 | 673 | 586 |
| 12 | 298 | 509 | 409 | 512 | 662 | 671 | 662 | 671 |
| 14 | 296 | 536 | 412 | 566 | 654 | 741 | 654 | 740 |
| >100 | 292 | 654 | 338 | 746 | 627 | 1005 | 632 | 1010 |

| | Test 9 2.0 kHz Quiet | | Test 10 2.0 kHz Loud | | Test 11 14.2 kHz Quiet | | Test 12 14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 544 | 137 | 633 | 190 | 773 | 340 | 773 | 340 |
| 2 | 530 | 131 | 638 | 192 | 796 | 335 | 797 | 336 |
| 4 | 553 | 169 | 654 | 223 | 835 | 356 | 833 | 357 |
| 6 | 569 | 249 | 685 | 294 | 874 | 421 | 874 | 422 |
| 8 | 585 | 359 | 645 | 382 | 865 | 499 | 865 | 499 |
| 10 | 599 | 473 | 630 | 487 | 811 | 607 | 811 | 607 |
| 12 | 605 | 555 | 631 | 569 | 802 | 697 | 802 | 697 |
| 14 | 612 | 621 | 631 | 635 | 797 | 773 | 797 | 772 |
| >100 | 612 | 850 | 623 | 862 | 774 | 1034 | 774 | 1033 |

| | Test 13 2.0 kHz Quiet | | Test 14 2.0 kHz Loud | | Test 15 14.2 kHz Quiet | | Test 16 14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 254 | 35 | 349 | 74 | 414 | 105 | 473 | 152 |
| 2 | 259 | 57 | 290 | 70 | 430 | 138 | 485 | 180 |
| 4 | 266 | 112 | 306 | 124 | 436 | 194 | 475 | 227 |
| 6 | 224 | 197 | 263 | 200 | 424 | 269 | 476 | 312 |
| 8 | 226 | 280 | 278 | 283 | 417 | 358 | 472 | 409 |
| 10 | 232 | 340 | 272 | 345 | 410 | 431 | 464 | 486 |

APPENDIX-continued

Test Results

| | | | | | | | | |
|---|---|---|---|---|---|---|---|---|
| 12 | 225 | 338 | 264 | 389 | 443 | 524 | 463 | 537 |
| 14 | 223 | 418 | 276 | 448 | 439 | 581 | 462 | 608 |
| >100 | 220 | 565 | 267 | 612 | 436 | 786 | 456 | 813 |

| | Test 17<br>2.0 kHz Quiet | | Test 18<br>2.0 kHz Loud | | Test 19<br>14.2 kHz Quiet | | Test 20<br>14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 328 | 67 | 415 | 114 | 641 | 276 | 637 | 274 |
| 2 | 334 | 100 | 428 | 145 | 666 | 326 | 661 | 316 |
| 4 | 334 | 176 | 438 | 208 | 679 | 409 | 674 | 385 |
| 6 | 297 | 257 | 459 | 310 | 681 | 487 | 676 | 478 |
| 8 | 298 | 351 | 490 | 372 | 663 | 579 | 660 | 574 |
| 10 | 304 | 422 | 420 | 462 | 646 | 664 | 645 | 662 |
| 12 | 299 | 467 | 405 | 518 | 640 | 730 | 647 | 737 |
| 14 | 296 | 506 | 427 | 592 | 632 | 793 | 640 | 801 |
| >100 | 292 | 659 | 432 | 793 | 624 | 1009 | 635 | 1022 |

| | Test 21<br>2.0 kHz Quiet | | Test 22<br>2.0 kHz Loud | | Test 23<br>14.2 kHz Quiet | | Test 24<br>14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 585 | 177 | 646 | 216 | 775 | 348 | 774 | 345 |
| 2 | 593 | 206 | 660 | 248 | 797 | 373 | 797 | 377 |
| 4 | 605 | 264 | 653 | 297 | 812 | 437 | 810 | 436 |
| 6 | 601 | 346 | 662 | 383 | 815 | 522 | 815 | 524 |
| 8 | 588 | 485 | 647 | 462 | 798 | 616 | 805 | 610 |
| 10 | 593 | 529 | 642 | 558 | 785 | 712 | 790 | 711 |
| 12 | 594 | 593 | 640 | 618 | 778 | 780 | 786 | 774 |
| 14 | 594 | 648 | 636 | 677 | 773 | 838 | 780 | 838 |
| >100 | 594 | 856 | 631 | 874 | 762 | 1040 | 771 | 1038 |

| | Test 25<br>2.0 kHz Quiet | | Test 26<br>2.0 kHz Loud | | Test 27<br>14.2 kHz Quiet | | Test 28<br>14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 256 | 50 | 293 | 68 | 417 | 134 | 463 | 173 |
| 2 | 256 | 93 | 317 | 129 | 416 | 200 | 458 | 242 |
| 4 | 257 | 170 | 285 | 192 | 408 | 296 | 456 | 350 |
| 6 | 224 | 259 | 260 | 280 | 410 | 396 | 447 | 439 |
| 8 | 229 | 327 | 265 | 351 | 412 | 488 | 452 | 531 |
| 10 | 229 | 383 | 263 | 406 | 438 | 578 | 461 | 610 |
| 12 | 224 | 426 | 263 | 457 | 439 | 629 | 452 | 646 |
| 14 | 225 | 466 | 258 | 492 | 439 | 671 | 455 | 692 |
| >100 | 222 | 582 | 255 | 615 | 440 | 809 | 458 | 833 |

| | Test 29<br>2.0 kHz Quiet | | Test 30<br>2.0 kHz Loud | | Test 31<br>14.2 kHz Quiet | | Test 32<br>14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 325 | 88 | 388 | 124 | 637 | 315 | 637 | 316 |
| 2 | 326 | 141 | 388 | 185 | 647 | 409 | 648 | 409 |
| 4 | 329 | 226 | 406 | 290 | 641 | 517 | 641 | 517 |
| 6 | 293 | 327 | 380 | 379 | 636 | 624 | 636 | 625 |
| 8 | 298 | 407 | 382 | 470 | 631 | 721 | 631 | 721 |
| 10 | 299 | 461 | 395 | 534 | 629 | 785 | 629 | 786 |
| 12 | 295 | 509 | 388 | 581 | 627 | 842 | 627 | 842 |
| 14 | 294 | 553 | 392 | 634 | 628 | 893 | 628 | 893 |
| >100 | 292 | 678 | 378 | 758 | 627 | 1038 | 627 | 1039 |

| | Test 33<br>2.0 kHz Quiet | | Test 34<br>2.0 kHz Loud | | Test 35<br>14.2 kHz Quiet | | Test 36<br>14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 578 | 204 | 636 | 245 | 777 | 383 | 777 | 386 |
| 2 | 548 | 248 | 644 | 326 | 790 | 474 | 791 | 474 |
| 4 | 570 | 366 | 620 | 406 | 786 | 580 | 786 | 579 |
| 6 | 572 | 462 | 622 | 499 | 783 | 675 | 783 | 675 |
| 8 | 594 | 556 | 628 | 585 | 781 | 760 | 781 | 760 |
| 10 | 606 | 636 | 625 | 654 | 778 | 836 | 778 | 836 |
| 12 | 608 | 690 | 624 | 705 | 777 | 889 | 777 | 888 |

APPENDIX-continued

Test Results

| | | | | | | | | |
|---|---|---|---|---|---|---|---|---|
| 14 | 607 | 734 | 628 | 754 | 776 | 933 | 776 | 933 |
| >100 | 610 | 878 | 623 | 891 | 774 | 1070 | 774 | 1070 |

| | Test 37<br>2.0 kHz Quiet | | Test 38<br>2.0 kHz Loud | | Test 39<br>14.2 kHz Quiet | | Test 40<br>14.2 kHz Loud | |
|---|---|---|---|---|---|---|---|---|
| Distance Mm | V1 (mV) | V2 (mV) | V1 (mV) | V2 (mV) | V1 (mV) | V2 (mV) | V1 (mV) | V2 (mV) |
| 0 | 325 | 71 | 405 | 115 | 636 | 286 | 637 | 287 |
| 2 | 330 | 98 | 417 | 146 | 659 | 326 | 659 | 327 |
| 4 | 341 | 166 | 428 | 208 | 671 | 398 | 671 | 398 |
| 6 | 296 | 259 | 423 | 295 | 673 | 488 | 673 | 489 |
| 8 | 294 | 342 | 405 | 378 | 658 | 578 | 658 | 578 |
| 10 | 301 | 403 | 407 | 447 | 639 | 659 | 640 | 660 |
| 12 | 297 | 442 | 412 | 500 | 632 | 716 | 632 | 716 |
| 14 | 293 | 475 | 408 | 549 | 626 | 768 | 627 | 768 |
| >100 | 290 | 600 | 403 | 695 | 619 | 943 | 619 | 943 |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of determining a position of an external transceiver relative to an implanted transceiver, the method comprising:
measuring the strength of a magnetic field proximal to the external transceiver, wherein the magnetic field is generated at least in part by the external transceiver; and
determining a position of the external transceiver relative to the implanted transceiver from said measured magnetic field strength.

2. The method according to claim 1 wherein determining comprises:
comparing a measured strength of magnetic field proximal to the external transceiver to a threshold value.

3. The method according to claim 2 further comprising:
indicating that the external transceiver has been displaced when the measured strength of magnetic field proximal to the external transceiver is greater than the threshold value.

4. The method according to claim 3 wherein indicating comprises:
providing an audible indication.

5. The method according to claim 1 wherein determining comprises:
mapping said measured magnetic field strength to a distance value.

6. The method according to claim 5 wherein mapping comprises:
consulting a look-up table comprising a plurality of pairs of values, each pair of values mapping a particular magnetic field strength to a corresponding transceiver separation distance.

7. The method according to claim 5 wherein mapping comprises:
algorithmically converting said measured value of magnetic field into a corresponding transceiver separation distance.

8. The method according to claim 1 further comprising:
providing a transcutaneous link between the external transceiver and the implanted transceiver, the link being bidirectional such that the external transceiver and the implanted transceiver transmit and receive signals across the transcutaneous link.

9. The method according to claim 8 further comprising:
transmitting power and data signals from the external transceiver to the implanted transceiver across the transcutaneous link.

10. The method according to claim 8 further comprising:
transmitting data signals from the implanted transceiver to the external transceiver across the transcutaneous link.

11. The method according to claim 1 further comprising:
providing a transcutaneous link between the external transceiver and the implanted transceiver, the link being unidirectional such that the external transceiver, comprising a transmitter, transmits signals to the implanted transceiver, comprising a receiver, across the transcutaneous link.

12. The method according to claim 11 wherein the signals transmitted by the transmitter are power and data signals.

13. The method according to claim 1 wherein measuring comprises:
positioning a pick-up coil proximal to the external transceiver such that a voltage induced on the pick-up coil is indicative of a magnetic field proximal to the external transceiver.

14. The method according to claim 13 further comprising:
the positioning the pick-up coil in a plane substantially perpendicular to a primary axis of the magnetic field, wherein the magnetic is produced between the external receiver and the implanted receiver.

15. The method according to claim 14 wherein the pick-up coil comprises an open-circuited single turn positioned concentrically with turns of the external receiver.

16. An apparatus for determining a position of an external transceiver relative to an implanted transceiver, the apparatus comprising:
means for measuring the strength of a magnetic field proximal to the external transceiver,
wherein the magnetic field is generated at least in part by the external transceiver; and
means for determining a position of the external transceiver relative to the implanted transceiver from said measured magnetic field strength.

17. The apparatus according to claim 16 further comprising means for comparing a measured strength of magnetic field proximal to the external transceiver to a threshold value.

18. The apparatus according to claim 17 further comprising means for indicating that the external transceiver has been displaced when the measured strength of magnetic field proximal to the external transceiver is greater than the threshold value.

19. The apparatus according to claim 18 wherein the means for indicating comprises any one of an audible alarm, or a visible indicator.

20. The apparatus according to claim 16 further comprising means for mapping a measured magnetic field strength proximal to the external transceiver to a distance value.

21. The apparatus according to claim 20 wherein the means for mapping comprises a look-up table comprising a plurality of pairs of values of magnetic field strength to transceiver separation distance.

22. The apparatus according to claim 20 wherein the means for mapping comprises means for algorithmically converting said measured value of magnetic field into a corresponding transceiver separation distance.

23. The apparatus according to claim 16 wherein the external transceiver and the implanted transceiver provide a transcutaneous link.

24. The apparatus according to claim 23 wherein the transcutaneous link comprises an RF link.

25. The apparatus according to claim 23 wherein the transcutaneous link is bidirectional such that the external transceiver and the implanted transceiver transmit and receive signals across the transcutaneous link.

26. The apparatus according to claim 25 wherein power and data signals are transmitted from the external transceiver to the implanted transceiver across the transcutaneous link.

27. The apparatus according to claim 25 wherein data signals are transmitted from the implanted transceiver to the external transceiver across the transcutaneous link.

28. The apparatus according to claim 23 wherein the transcutaneous link is unidirectional, the external transceiver comprises a transmitter and the implanted transceiver comprises a receiver, such that the transmitter transmits signals to the receiver across the transcutaneous link.

29. The apparatus according to claim 28 wherein the signals transmitted by the transmitter are power and data signals.

30. The apparatus according to claim 16 wherein the means for measuring the strength of the magnetic field proximal to the external transceiver comprises a pickup coil positioned proximal to the external transceiver, such that a voltage induced on the pickup coil is indicative of a magnetic field proximal to the external transceiver.

31. The apparatus according to claim 30 wherein the pickup coil is positioned in a plane substantially perpendicular to a primary axis of the magnetic field and wherein the magnetic field is produced by the transceivers.

32. The apparatus according to claim 31, wherein the external transceiver comprises a transmitter coil comprising turns and wherein the pickup coil comprises an open circuited single turn positioned concentrically with turns of the external transceiver.

33. The apparatus according to claim 30, further comprising:
    peak detector means; and
    wherein an output of the pick-up coil is passed through the peak detector means.

34. An apparatus for determining a position of an external transceiver relative to an implanted transceiver, the apparatus comprising:
    means for measuring the strength of a magnetic field proximal to the external transceiver;
    means for determining a position of the external transceiver relative to the implanted transceiver from said measured magnetic field strength;
    means for comparing a measured strength of magnetic field proximal to the external transceiver to a threshold value;
    means for indicating that the external transceiver has been displaced when the measured strength of the magnetic field proximal to the external transceiver is greater than the threshold value; and
    means for mapping comprises a look-up table comprising a plurality of pairs of values of magnetic field strength to transceiver separation distance.

* * * * *